United States Patent [19]

Meador et al.

[11] Patent Number: 5,549,141

[45] Date of Patent: Aug. 27, 1996

[54] LIQUID CONTAINER SAMPLE TRANSFER METHOD AND APPARATUS

[75] Inventors: James W. Meador; Thomas L. Kraft; Thomas G. Miller, all of Houston, Tex.

[73] Assignee: KVM Technologies, Inc., Houston, Tex.

[21] Appl. No.: 276,892

[22] Filed: Jul. 19, 1994

[51] Int. Cl.$^6$ ................................ B65B 1/04; B65B 3/04
[52] U.S. Cl. .............................. 141/1; 141/26; 141/98; 141/114; 141/130; 422/63; 436/180; 73/863.84
[58] Field of Search .................................. 141/1, 25, 26, 141/27, 81, 82, 98, 114, 117, 130; 422/63; 436/180; 222/214, 81, 82, 152; 73/863.81, 863.83, 863.84

[56] References Cited

U.S. PATENT DOCUMENTS

| | | | |
|---|---|---|---|
| 4,690,017 | 2/1986 | Coulter et al. ............................... | 141/1 |
| 5,069,364 | 12/1991 | McGill ...................................... | 222/95 |
| 5,411,065 | 5/1995 | Meador et al. ............................... | 141/1 |

Primary Examiner—Henry J. Recla
Assistant Examiner—Steven O. Douglas
Attorney, Agent, or Firm—Tim L. Burgess

[57] ABSTRACT

A method for dispensing a sample of liquid from a sealed thermoplastic container which includes both a volumetrically flexible chamber holding the liquid and also a plurality of spaced axially vertical nozzles on the container underside, the nozzles having an inlet in fluid communication with the chamber. The container is first manipulated to increase the volume of the chamber, rotated from a right side up position to an upside down position, and after the two preceding operations an axial opening is non-invasively created in the nozzle while the container is upside down without decreasing the volume of the chamber. The container is then rotated from the upside down position to a right side up position without decreasing the volume of the chamber, manipulated to decrease the volume of the chamber and expel a sample of the liquid from the chamber through the nozzle opening, then rotated to an upside down position and the opening in the nozzle is closed by melting and clamping it closed.

20 Claims, 7 Drawing Sheets

LIQUID CONTAINER SAMPLE TRANSFER METHOD AND APPARATUS

FIELD OF THE INVENTION

The present invention relates generally to the field of liquid sampling and testing and most particularly to urine specimen collection devices and apparatus for processing urine for substance abuse testing.

BACKGROUND OF THE INVENTION

In fields such as clinical medicine, forensic sciences, environmental quality testing, food quality assurance, drug testing, and other areas, it has become possible to determine the presence and/or amount of trace substances in test samples even when such substances are present in very low concentrations (on the order of parts per million and parts per billion). Substance abuse has given rise to widespread urine specimen testing. Positive test results identifying an illicit substance in a specimen may have a profound impact on the donor's career or employment. In the proper circumstances, positive test results may also result in criminal liability for the donor. As another example, the U.S. Environmental Protection Agency conducts a variety of ongoing testing programs. These testing programs are intended to guarantee compliance with standards for maximum levels of toxic and/or radioactively contaminated fluids, such as plant effluent, and results of tests can figure in civil and criminal liabilities.

Particularly in the area of testing for substance abuse, large and increasingly high volumes of urine testing has created a need for specialized specimen collection containers and apparatus for transferring liquids from specimen collection containers without adulterating either the sample removed or the liquid remaining in the container. Thus, there has been a need for a liquid specimen collection container that provides for more than one isolated specimen of a sample to provide redundancy for third party confirmation testing, that automatically retains an archival specimen so that tests may be repeated on the identical specimen and the results of the screening tests either verified or disproved, and that cannot be accessed without evident tamper. Providing these benefits, embodiments of a specimen collection container device invention have been described which eliminates human contact with the specimen once the specimen is sealed in the device and which provides split specimen collection. These descriptions are set forth in pending U.S. patent application Ser. No. 08/180,872 filed Jan. 11, 1994, entitled "Fluid Sample Receptacle", incorporated herein by reference as if set forth verbatim, and in its parent application Ser. No. 08/027,860, filed Mar. 8, 1993, now abandoned.

Apparatus is described in U.S. patent application Ser. No. 08/179,436, filed Jan. 10, 1994, for automated sampling to obtain aliquots from specimen collection devices that have certain features of devices described in U.S. patent application Ser. No. 08/180,872 and herein. The aliquots are used for high volume screening and verification tests.

However urine testing facilities that do not have the testing volume to support an automated sampling apparatus as described in U.S. patent application Ser. No. 08/179,436 need a method and apparatus for removing samples of urine from a container such as described in U.S. patent application Ser. No. 08/180,872 and herein. This invention is directed to that need.

SUMMARY OF THE INVENTION

This invention comprises a method and means for dispensing a sample of liquid from a sealed thermoplastic container which includes both a volumetrically flexible chamber holding the liquid and also a plurality of spaced axially vertical nozzles on the container underside, the nozzles having an inlet in fluid communication with the chamber. The method comprises the operations of (a) rotating the container from a right side up position to an upside down position, (b) before or after step (a) and before step (c), manipulating the container to increase the volume of the chamber, (c) creating an axial opening in the nozzle while the container is upside down without decreasing the volume of the chamber, (d) rotating the container from the upside down position to a right side up position without decreasing the volume of the chamber, (e) manipulating the container to decrease the volume of the chamber, thereby to expel a sample of the liquid from the chamber through the nozzle opening, (f) rotating the container from the right side up position to an upside down position, and (g) closing the opening in the nozzle while the container is in the upside down position. Suitably, after step (e) and before the step (f), the container is manipulated to increase the volume in the chamber, and in step (a) the container is rotated such that the nozzle to be opened is at a sufficient angle from vertical that air trapped in the chamber gathers at the inlet to the nozzle. To prevent adulteration of the sample or the liquid remaining in the container, the opening in the nozzle and the closing of the opening is performed non-invasively, such as with a stream of heated air or a laser beam. The manipulation step (b) is suitably performed by pulling on at least one other nozzle than the nozzle opened in step (c), and the manipulation step (e) suitably is performed by pushing on a bellows portion of the container, preferably on at least one other nozzle than the nozzle opened in step (c).

Thus, apparatus for conducting the operations of the method of this invention includes means for rotating the container from a right side up position to an upside down position and for rotating the container from the upside down position to a right side up position, means for creating an axial opening in the nozzle, means for manipulating the container to increase the volume of the chamber before or after rotating the container from a right side up position to an upside down position and for manipulating the container to decrease the volume of the chamber after opening of the nozzle, and means for closing the opening in the nozzle. Suitably the means for rotating the container from right side up to upside down comprises means for rotating the container such that the nozzle to be opened is at a sufficient angle from vertical that air trapped in the chamber gathers at the inlet to the nozzle, and the means for creating an opening in the nozzle comprises means for non-invasively creating the opening, as by means for providing a stream of heated air or means for providing a laser beam. Suitably also, the means for manipulating the container to increase the volume of the chamber comprises means for pulling on at least one other nozzle than the nozzle to be opened, and the means for manipulating the container to decrease the volume of the chamber comprises means for pushing on at least one other nozzle than the nozzle to be opened. To avoid adulteration, the means for closing an opening in the nozzle comprises means for non-invasively closing the opening, and may include means for non-invasively heating the opened nozzle adjacent the created opening sufficiently to make the nozzle molten, and means for compressing the nozzle adjacent the molten portion to fuse the nozzle closed.

These and other aspects of the invention will be more fully understood by reference to the drawings of a preferred embodiment and the related description that follows.

DESCRIPTION OF PREFERRED EMBODIMENTS

The method and apparatus of this invention are especially suited for obtaining a sample of a liquid sealed in a thermoplastic container which includes both a volumetrically flexible chamber holding the liquid and also a plurality of spaced axially vertical nozzles on the container underside, the nozzles having an inlet in fluid communication with the chamber. Several such container embodiments are described in pending U.S. patent application Ser. No. 08/180,872, filed Jan. 11, 1994, entitled "Fluid Sample Receptacle", incorporated herein by reference as if set forth verbatim, and in its parent application Ser. No. 08/027,860, filed Mar. 8, 1993. An example of such a container is depicted in FIG. 12.

Figure 12:
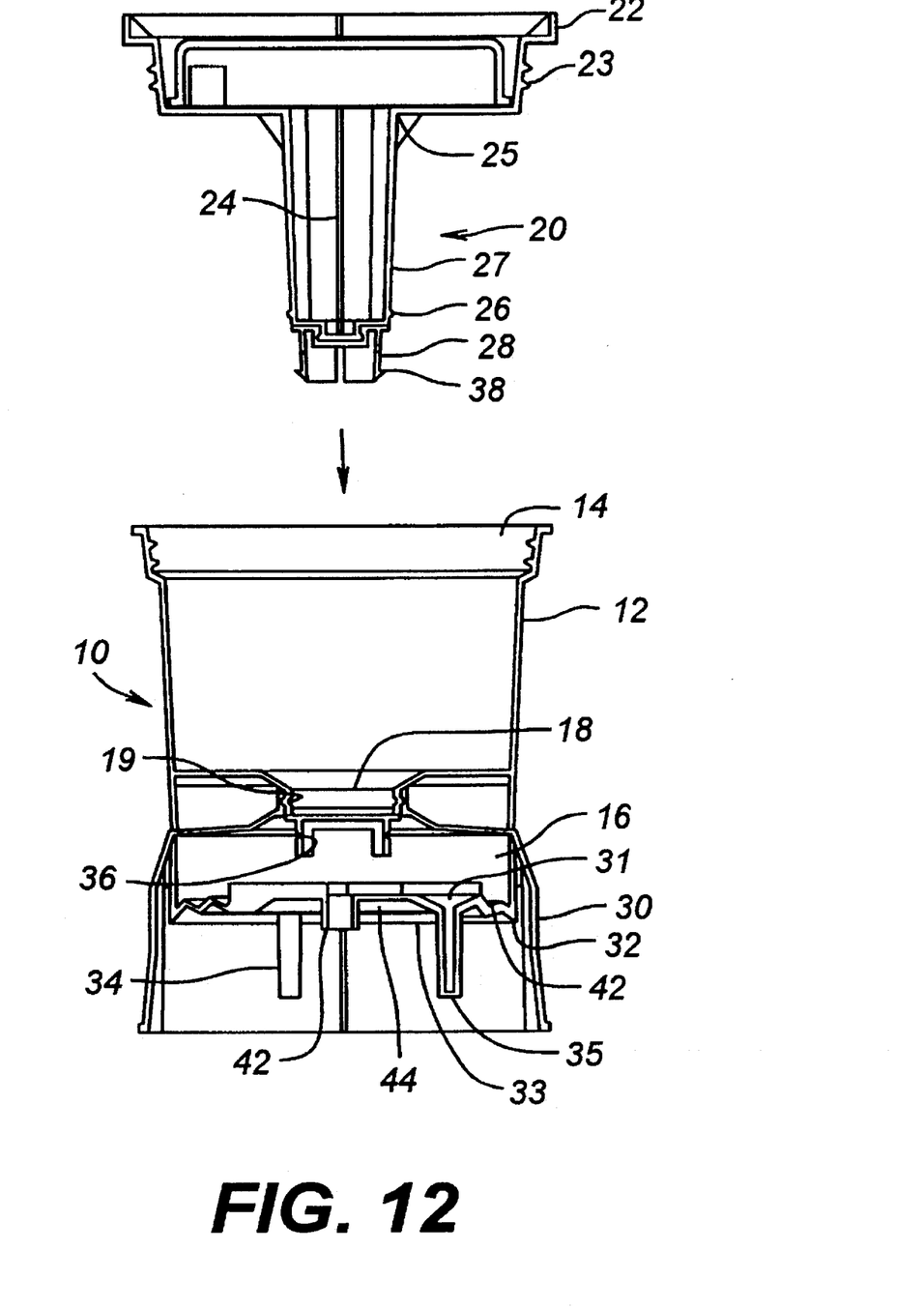
FIG. 12 is a longitudinal axial section of the closure and receptacle of a liquid specimen container usable with the apparatus of this invention according to the method of this invention.

Referring to FIG. 12, a liquid specimen collection container indicated generally by reference numeral 10 comprises an upper sample chamber 12 having an upper access opening 14, a lower sample chamber 16 releasably engageable with the upper sample chamber 12, a flow passage 18 connecting upper chamber 12 and lower chamber 16 to conduct liquid from the upper sample chamber 12 to the lower sample chamber 16, and a container closure and seal generally indicated by reference number 20, engageable with the upper sample chamber 12 to close upper access opening 14 and seal upper sample chamber 12 and lower sample chamber 16 adjacent the flow passage 18. The container closure or top 20 comprises a lid 22, sealingly engageable with upper sample chamber 12, suitably as by exterior threads 23 on lid 22 and interior threads on chamber 12. Container closure 20 further comprises a vertical column 24 joined to lid 22 at a first end 25 of the column, an upper plug portion 26 of the column at a second end 27 of the column sealingly engageable with upper sample chamber 12 adjacent passage 18 in an upper portion 19 thereof, and a lower plug 28, releasably joined to the upper plug portion 26 to seal the lower sample chamber 16. Lower sample chamber 16 comprises a base 30, a variable or flexible volume bellows portion or assembly 32 joined to base 30 and a retaining element 36, suitably in the form of an annular keeper groove, to cooperatively engage a mating element 38, in the form of a projecting annular rim, on lower plug 28. Bellows portion or assembly 32 comprises a bellows 42, floor plate portion 33 radially inward from bellows 42, and a plurality of spaced substantially axially vertical access apertures or nozzles 34 in a lower portion of floor plate portion 33. Three nozzles 34 (two are visible in the section) are spaced 120 degrees apart. The nozzles have a duct 34 opening into lower sample chamber 16 of container 10, and also have a closure 35 closing the duct remotely from the duct opening into the chamber 16. A guide recess 40 is formed centrally in the underside of bellows assembly 32. A tamper evident seal may be placed over lid 22 onto the outside of upper and lower sample chambers 12 and 16, and another seal may be placed across the mouth of base 30.

At a place of specimen collection a container 10 and a closure 20 are removed from a sealed wrapper. In a typical chain-of-custody procedure, the donor, typically after completing a multicopy requisition, is given container 10. The specimen donor privately urinates into container 10 through upper opening 14. Urine flows from upper chamber 12 through flow passage 18 into lower chamber 16, fills the lower chamber 16 and rises into upper chamber 12. The shape of lower chamber 16 allows a few milliliters of air to trap at the ceiling of lower chamber 16.

The donor returns the vessel assembly to the collector, who inserts closure 20 and closes upper opening 14, by screwing lid 22 onto threads 36. This action also seats upper plug 26 in portion 19 of passage 18, thereby sealing upper chamber 12 at passage 18, and seats rim 38 of lower plug 28 in retaining element 36 of base 30, sealing lower chamber 16 at passage 18. Tamper evident seal 52 already is in place across base 30. The collector suitably may place a tamper evident tape 50 across lid 22 and onto the sides of container 10. The donor typically initials tape 50.

For delivery to a testing laboratory, typically container 10 is placed in one compartment of a two compartment mailing pouch. The requisition is typically signed by the donor and collector, a copy of it is given to the donor and a file copy is retained by the collector. The remainder of the requisition typically is placed in the second compartment of the pouch. The pouch is then sealed and delivered to a testing laboratory, where a specimen or aliquot of the specimen in the vessel assembly will be removed for analytical testing. Bellows assembly 32 permits lower chamber 16 to expand or contract upon exposure of the vessel assembly to any materially lower or higher ambient pressure either during transit or at the destination. Bellows assembly 32 therefore assures that the ambient pressure changes to which container 10 is exposed do not cause the vessel to leak.

At the destination, the testing laboratory continues assurance of chain-of-custody of the vessel assembly. Typically a technician removes the vessel assembly and the requisition from the pouch and attaches identical bar code labels from a set, one to the requisition, one to container 10. The tamper proof tape 50 is then removed from container 10, exposing base 30. Vessel assembly 10 is now ready for removal of an aliquot from the split urine specimen sealed in the lower chamber 16.

Figure 1:
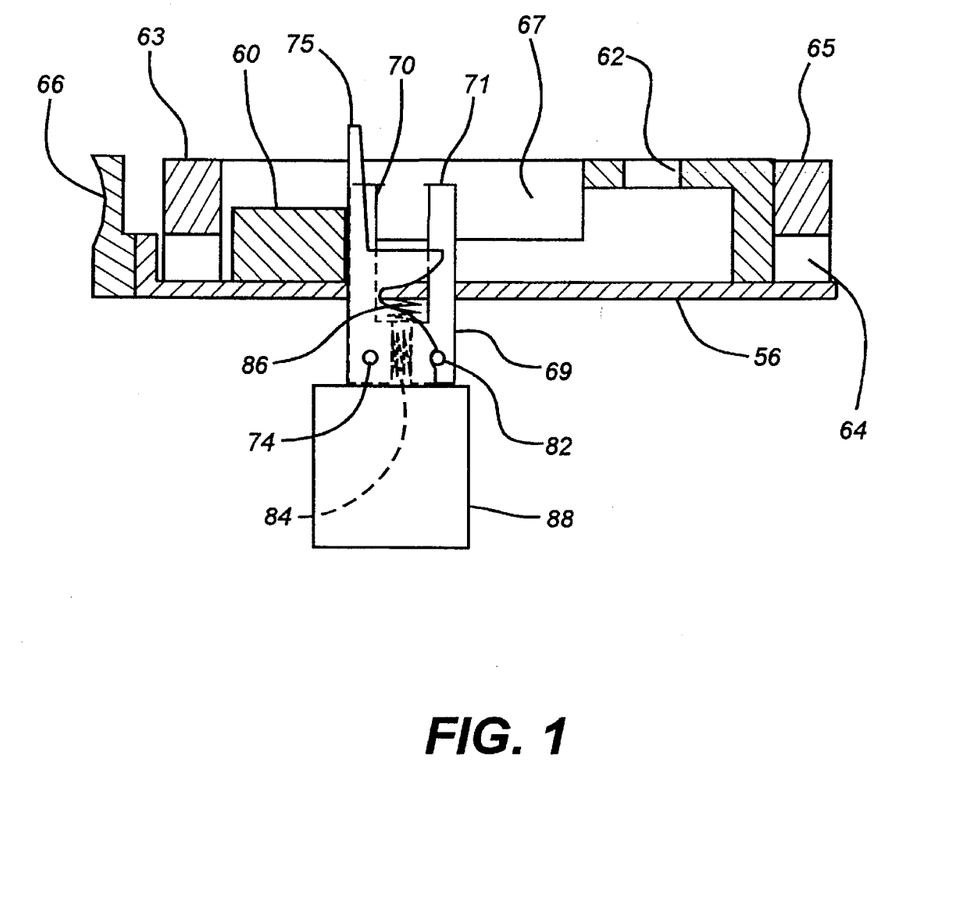
FIG. 1 is a front sectional schematic view of a portion of the apparatus for conducting a portion of the operations of this invention.
Figure 2:
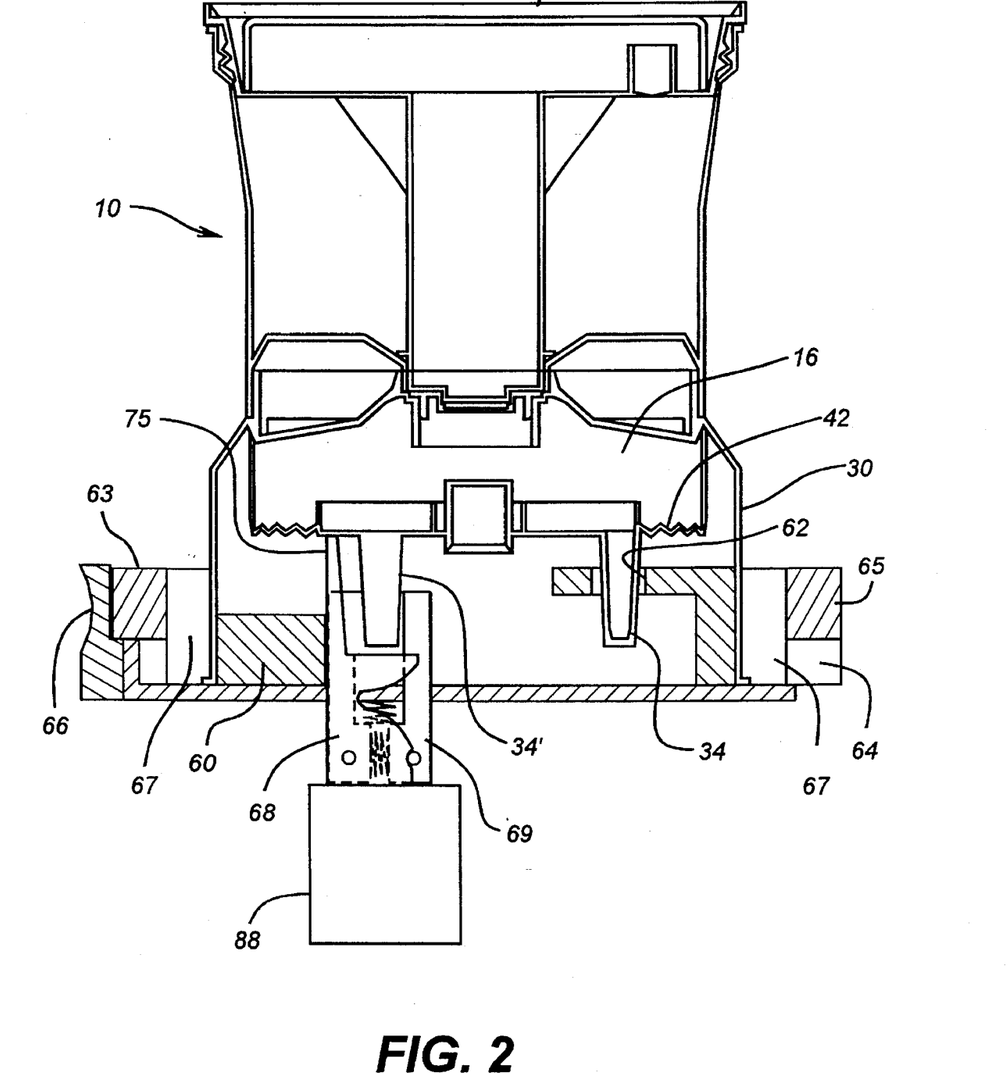
FIG. 2 is a front sectional view as in FIG. 1, also depicting a longitudinal sectional view of a container of the type designed to be operated upon by the method and apparatus of this invention.
Figure 3:
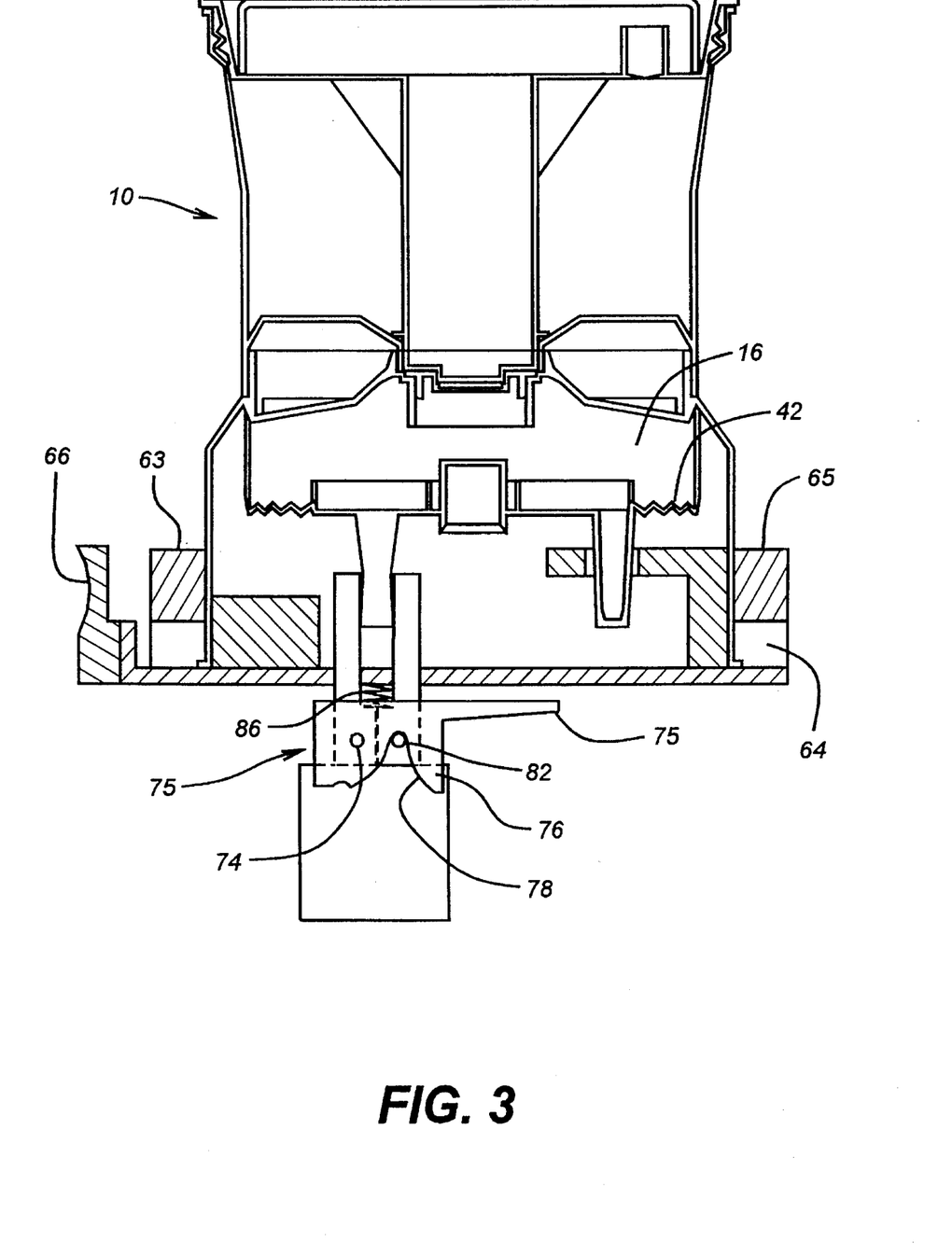
FIG. 3 is a view in the same orientation of FIG. 2.

Referring to FIGS. 1, 2, and 3, the method by which container 10 is aligned and held in the apparatus of this invention is illustrated. An annular base 56 supports a container holding ring 60 having a circular interior periphery fitting within the interior periphery of container 10. On the right side of the viewer, container holding ring 60 has a cutout 62 for receiving a nozzle 34. The purpose of cutout 62 is to accurately position nozzle 34 for subsequent operations which will take place on the nozzle. A hinge lock 64 is mounted on annular base 56, and comprises a left portion 63, as viewed in FIGS. 1–3, and a right portion 65, as viewed in FIGS. 1–3, interconnected by a spring action 67. A fixed grip 66 is mounted to the left of left hinge lock portion 63, as viewed in FIGS. 1–3. To fit container 10 upon annular base 56, an operator grasps left hinge lock 63 and fixed grip 66. By squeezing left hinge lock 63 toward fixed grip 66, the interconnecting spring action 67 to right hinge lock 65 opens a space between ring 60 and left and right hinge locks 63 and 65. Container 10 is then aligned and set into place, as seen in FIG. 2. After the operator has positioned container 10 as shown in FIG. 2, left hinge lock 63 is released. The spring action 67 closes left hinge lock 63 and right hinge lock 65 on the outside periphery of container 10, locking container 10 into position.

As described above, lower sample chamber 16 will contain urine and air. The pressures within lower sample chamber 16 may be above local ambient pressures at the testing laboratory. It is a requirement that, when container 10 is violated for sampling, the liquid contents not forcibly exhaust from the container due to a pressure differentially higher inside chamber 16 than outside ambient pressure. Not only would an expulsion of liquid lessen specimen available for sampling, but more seriously, the apparatus for conducting the operations on the container 10 would be contaminated. Measures are desirable to avoid a possibly of cross contamination of a future sample from trace residues on the apparatus 10. These considerations require a pressure manipulation of lower chamber 16 be performed.

FIGS. 1, 2 and 3 depict a mechanism comprising two portions for manipulating container 10 to decrease the volume of lower chamber 16. One portion of the mechanism grips at least one nozzle 34' other than the nozzle 34 set in cutout 62. More particularly, a pair of arms 68 and 69 are vertically slideably mounted to annular base 56. Arms 68 and 69 include a pair of upstanding finger portions 70 and 71. In FIGS. 1–3, the arms are perpendicular to the plane of the paper, and fingers 70 and 71 are seen in end view in the plane of the paper. A latch 72 pivots around a left pin 74 which is attached to left finger 70. Latch 72 is depicted only in outline form so that the structure behind it can be seen. Latch 72 is best seen in FIG. 3. Latch 72 has a handle portion 75 and below the handle portion has a flag portion 76 with a curved right border 78 retreating inwardly in the direction of the handle portion 74 and providing a cam path as described presently. Right finger 71 has a right pin 82. Between left arm 68 and right arm 69 is a spring 84. Spring 84 provides a force to move left arm 68 and right arm 69 away from each other. When container 10 is placed in position as indicated in FIG. 2, the two nozzles 34' that are not the nozzle 34 placed in cutout 62 are aligned vertically between left arm 68 and right arm 69. When latch 72 is moved clockwise about left finger pin 74, as indicated in FIG. 3, right finger pin 82 camingly follows the path of border 78 of latch 72, pulling fingers 70 and 71 and accordingly arms 68 and 69 toward each other against the force of spring 84. This presses arms 68 and 69 against the nozzle or nozzles 34' aligned between arms 68 and 69, until border 78 comes into a stop on right pin 82 at a retreat terminus 79 of path 78. The nozzle or nozzles 34' pressed between arms 68 and 69 are thus "captured."

The other part of the mechanism for manipulating container 10 to decrease the volume of lower chamber 16 comprises a coil spring 86 located between annular base 56 and arms 68 and 69. In the container loading position illustrated in FIGS. 1–3, arms 68 and 69 rest on a stop 88 at the lower end of vertical travel of annular base 56, compressing coil spring 86. Spring 86 is compressed during the operation in which latch 72 is closed to catch and hold the captured nozzles 34'. When annular base 56 is raised vertically off stop 88, arms 68 and 69 are forced vertically downward by action of coil spring 86 released from compression. This downward movement of arms 68 and 69 pulls down the captured nozzles 34' held between arms 68 and 69, in turn drawing downwardly the flexible bellows assembly 32 of container 10. This expands the bellows 42 and enlarges the volume of lower chamber 16 of container 10. Because chamber 16 is sealed, this increase in chamber volume reduces the intra-chamber pressure relative to ambient pressure.

Thus, in the embodiment depicted in FIGS. 1–3 for the step of manipulating the container to increase the volume of chamber 16, the manipulation includes an element of vertically upward movement of annular base 56.

Another aspect of the method of this invention and apparatus 10 for implementing the method is that the container be placed in an upside down position to open the nozzle 34 placed in the cutout 62. This is especially desirable when the opening is to be made non-invasively, by heated air, in order that hot air jetted from a hot air pencil is made to flow downwardly. Orienting the jet downwardly limits container melting to the nozzle tip area, assisted by convection rise of less dense heated air. Also, ancillary mechanism of the apparatus is not heated by rising hot air currents as by contrast the mechanism would be if the hot air pencil were pointing up, the container were right side up, and the nozzle tip were to be opened by an upward jet of hot air.

Additionally, it is preferred to have container 10 oriented upside down so that air trapped in lower chamber 16 will rise to the top and collect below the inlet of the nozzle 34 to be opened. This provides an additional measure aiding prevention of adulteration of the apparatus, because, if the pressure manipulation step to reduce intra-chamber pressure should leave some slight positive differential pressure in the chamber relative to atmospheric, then only the entrapped air gathered beneath the nozzle inlet will exhaust instead of liquid in the chamber, when lower chamber 16 is accessed for sampling.

Accordingly, a step in the method of this invention is rotating the container from a right side up position to an upside down position. Preferably, in order to position any air trapped inside chamber 16 beneath the nozzle 34 to be opened, the container 10 is rotated such that the axis of nozzle 34 to be opened is at a sufficient angle from vertical that air trapped in chamber 16 gathers at the inlet to this nozzle. Suitably, a rotation 170° to 175° from right side up, putting the nozzle to be opened on the half of the annular base 56 elevated upside down 5° to 10° above horizontal, will suffice. Rotation suitably is accomplished in combination with a vertical motion alternatively by a rotational pneumatic cylinder atop a vertical pneumatic cylinder, by a mechanical rotational drive coupled to a linear drive, or by a vertical drive with an escapement which forces rotation.

For use with the apparatus elements depicted in FIGS. 1–3, this rotation step is preceded by the manipulation step described above in reference to FIGS. 1–3 to increase the volume of the lower chamber 10. A more sophisticated embodiment could effect the manipulation step after the rotation step, by appropriate electomechanical means traveling with annular base 56. Thus, before or after the rotation step and before the opening step described next, the container is manipulated to increase the volume of the chamber.

Figure 4:
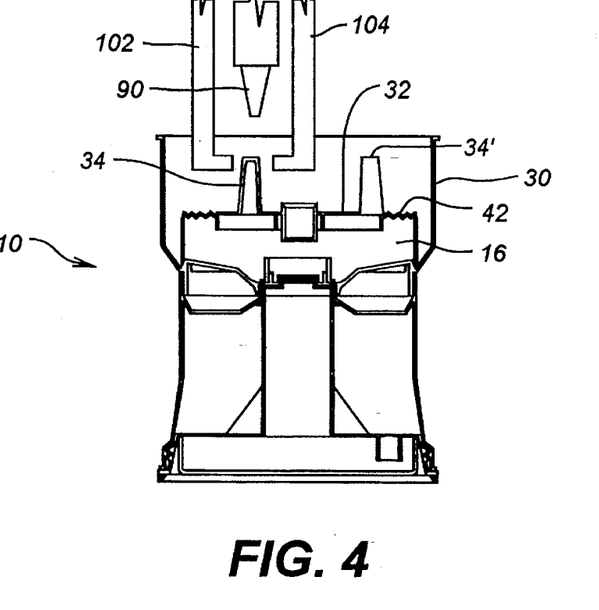
FIG. 4 is an schematic longitudinal section of the container seen in FIGS. 2 and 3 shown in schematic position for a container nozzle opening operation.

Referring to FIG. 4, container 10 is illustrated in upside down position after the rotation referred to in the immediately preceding paragraph. The apparatus schematically depicted in FIGS. 1–3 is not illustrated, for clarity, but the reference numbers will provide orientation for the structure that will be understood as present. Thus, nozzle(s) 34' will be understood to be locked between arms 68 and 69, and nozzle 34 will be understood kept in cutout 62. In the upside down position, nozzle 34 is illustrated substantially axially aligned under the orifice of a hot air pencil 90 oriented to stream hot air down toward the tip of nozzle 34 to open the nozzle by melting a small hole at the end of the nozzle. In the rotation to upside down position and in placement below hot air pencil 90, spring 86 remains extended, maintaining the volume increase in chamber 16 imparted by the manipulation described above. Thus, when a hole is opened in the tip of nozzle 34, breaching the separation between chamber 16 and the atmosphere, none of the liquid in chamber 16 is expelled. Actually, in many instances not only will the pressure in chamber 16 not be differentially greater than ambient before the nozzle opening is created, it also will be less than atmospheric. As a result, ambient outside air will enter the opening, and the rush of that air and any air bubbles formed by surface tension in nozzle duct 34 combine to provide another means of preventing liquid in chamber 16 from expelling onto the apparatus when the nozzle opening is created.

Also depicted schematically in FIG. 4 are crimper arms 102 and 104, described more particularly below in connection with FIGS. 6 and 9. In an embodiment where the hot air pencil 90 and the crimper arms 102 and 104 are vertically stationary, an element of vertical upward movement is required in addition to the element of rotational movement in order to position the nozzle between the crimper arms and at the correct distance from the hot air pencil orifice.

Figure 5:
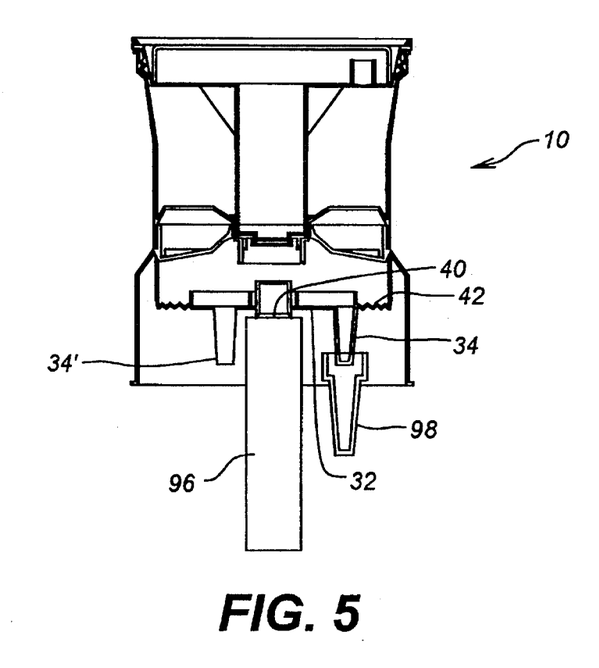
FIG. 5 is a schematic longitudinal section of the container seen in FIG. 4 shown in schematic position for a sample dispensing operation.

After an axial opening is created in nozzle 34, container 10 is rotated from the upside down position back to the right side up position in order to dispense a sample of liquid in chamber 16 into a receptacle. FIG. 5 schematically illustrates container 10 repositioned in the upright position. Again for clarity, components schematically depicted in FIGS. 1–3 are omitted but will be understood present. In the rotation back to right side up position, spring 86 remains extended, maintaining the volume increase in chamber 16 imparted by the manipulation described above in connection with FIGS. 1–3.

After rotation back to right side up position, in accordance with the method of this invention, container 10 is manipulated to decrease the volume of chamber 16 in order to expel liquid sample from the chamber, through the created nozzle opening into a receptacle for the sample. This is accomplished in the embodiment illustrated by vertical downward movement of container 10 after rotation of container 10 to a right side up position. Referring to FIG. 5, as container 10 in right side up position moves vertically downward, it strikes a fixed vertical member 96 positioned to impinge preferably at the center of bellows assembly 32, suitably on the rim of guide recess 40. This displaces bellows assembly 32 vertically upward a finite amount predetermined relative to the end of travel of the vertical descent of container 10 and the upward reach of vertical member 90, effective to discharge a desired quantity of liquid from chamber 16 into the receptacle 98 positioned to receive the dispensed liquid.

After a sample is dispensed from container 10, container 10 on annular base 56 is again rotated from the right side up position to an upside down position. In the embodiment illustrated, annular base 56 is moved vertically upward to clear it from member 98 and is then rotated. The upward movement frees bellows assembly 32 from vertical member 90 and results in an expansion of bellows 42 to the position permitted by the capture of nozzles 34' described in connection with FIGS. 1–3. The volume of chamber 16 is increased by the expansion of bellows 42, and air enters nozzle 34 and chamber 16 to equilibrate pressure. This clears the nozzle of any drops and prevents any discharge of liquid during the rotation maneuver. After rotation to the upside down position, the container completes its upward travel to a position depicted in FIGS. 6 and 9.

Figure 6:
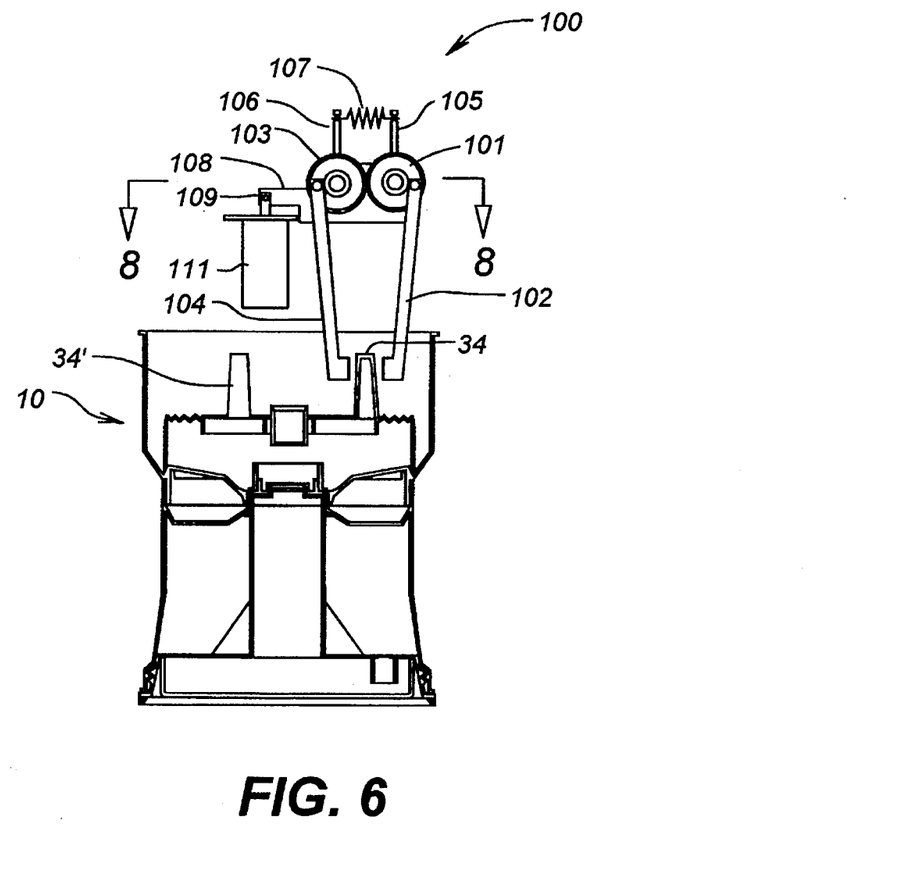
FIG. 6 is a schematic longitudinal section of the container seen in FIG. 5 in position for a nozzle closing operation depicted in side elevational view.
Figure 7:
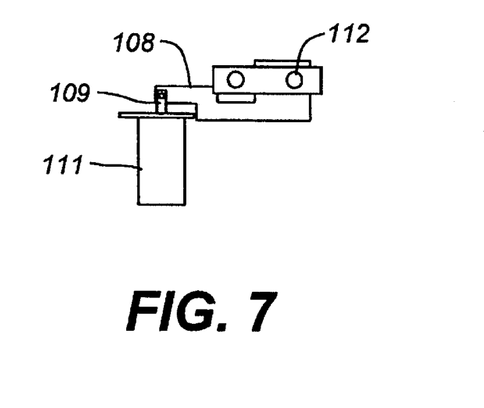
FIG. 7 is a from elevational view of a portion of the apparatus employed in the operation depicted in FIG. 6.
Figure 8:
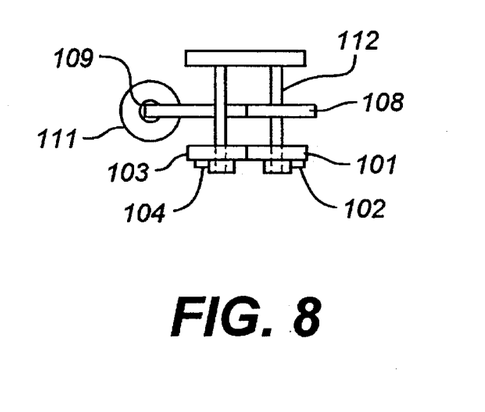
FIG. 8 is a schematic top plan view of a portion of the apparatus employed in the operation depicted in FIG. 6, viewed along the line 8—8 of FIG. 6.
Figure 9:
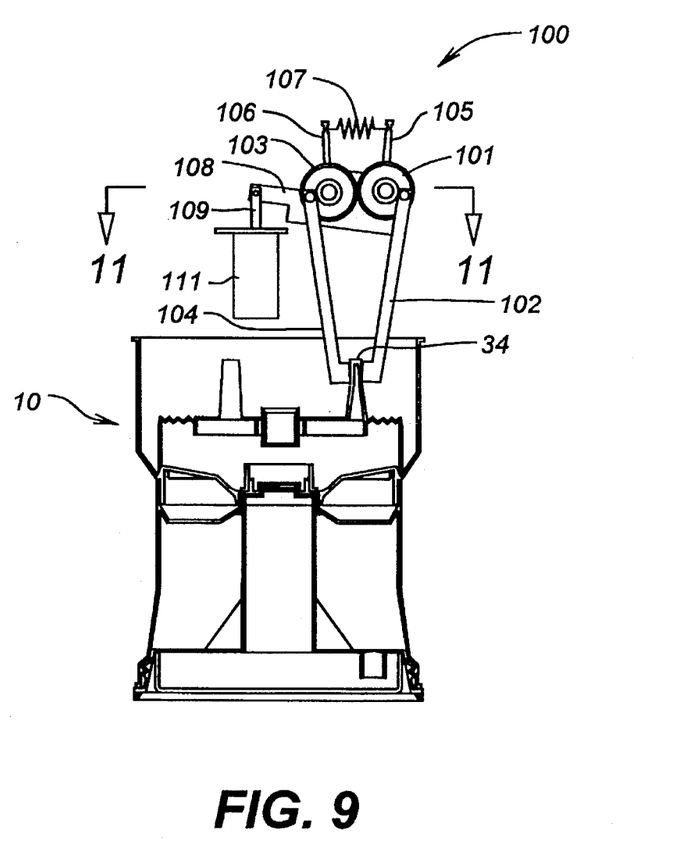
FIG. 9 is a schematic longitudinal section of the container seen in FIG. 6 in position in a nozzle closing operation depicted in side elevational view.

Referring to FIGS. 6 and 9, FIG. 6 depicts a front schematic view of a mechanical crimping mechanism 100. Hot air pencil 90 is not shown for clarity. A drive gear 101 has an arm 102 mounted to it. A driven gear 103 has a mirror image arm 104 mounted to it. Pins 105 and 106 extend from the top of gears 101 and 103 respectively, and are interconnected with spring 107. An actuation arm 108 is best viewed in FIG. 7, which is a front view of the crimping mechanism 101, with gears 101 and 103, arms 102 and 104, pins 105 and 106, and spring 107 not illustrated for clarity. Attached to the left hand side of actuation arm 108, as viewed, is a solenoid plunger 109 and solenoid 111. Attached to the right hand side of actuation arm 108 is a drive pin 112 which connects to drive gear 101.

In the normal mode of operation the mechanical crimping system is as indicated in FIG. 6. Spring 107 pulls pins 105 and 106 inward, which keeps gear 101 preferentially counterclockwise loaded, and keeps gear 103 preferentially clockwise loaded. Solenoid 111 is not energized. The result is that arms 102 and 104 are kept a fixed distance apart.

Figure 10:
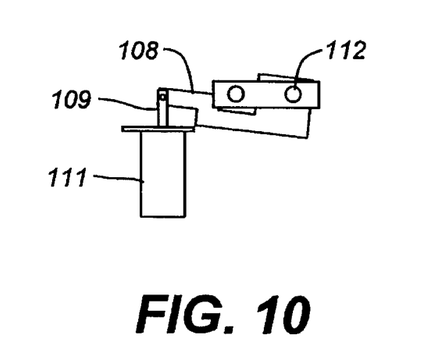
FIG. 10 is a front elevational view of a portion of the apparatus employed in the operation depicted in FIG. 9.
Figure 11:
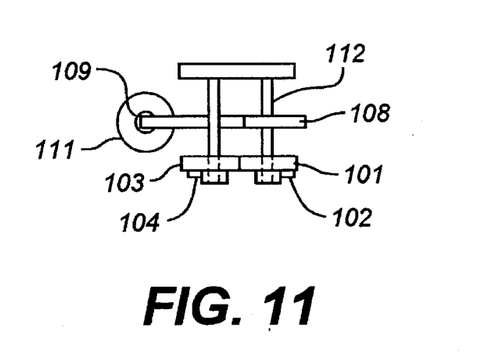
FIG. 11 is a schematic top plan view of a portion of the apparatus employed in the operation depicted in FIG. 9, viewed along the line 11—11 of FIG. 9.

During the sealing process, container 10 is elevated and oriented in the position indicated in FIG. 6 and 9. Air pencil 90, not shown, is energized, and the tip of nozzle 34 adjacent the created opening is remelted. After a predetermined time, hot air pencil 90 is de-energized and the crimping operation begins. This is best viewed in FIG. 9. Solenoid 111 is electrically energized, causing solenoid plunger 109 to move upward, as seen in FIG. 10. This movement causes actuation arm 108 to rotate clockwise. Because actuation arm 108 is connected to drive pin 112, which, in turn, is connected to gear 101, drive pin 112 and gear 101 also rotate clockwise. Clockwise rotation of gear 101 also causes clockwise rotation of arm 102. Gear 103 which is mechanically engaged with gear 101 rotates counterclockwise with the clockwise rotation of arm 104 coupled to it. Arms 102 and 104 then come together with sufficient force to overcome the restorative force of spring 107, and compress nozzle 34. The compression action of arms 102 and 104 on nozzle 34 closes the opening previously created, and seals container 10. At the end of the cycle, solenoid 111 is de-energized and under the restorative force of spring 107 the assembly returns to the configuration indicated in FIG. 6. Because the hot air stream of hot air vessel 90 is directed only on the area adjacent the previously created hole in the nozzle tip, arms 102 and 104 touch only non-melted plastic, and are thereby maintained clean of melted plastic residue.

After the created opening in nozzle 34 is closed, the container is released and removed from the apparatus. Latch 72 is opened to the position seen in FIGS. 1 and 2, allowing spring 84 to separate arms 68 and 69 and release nozzles 34'. Left hinge lock 63 is then moved toward fixed grip 66 to open right and left hinge locks 63 and 65, allowing container 10 to be removed from annular base 56.

Instead of the hot air pencil 90 used in the above embodiments, a laser beam may be employed to open and seal the nozzle of the liquid specimen container. A Laser power supply and electrocontroller are controlled to electromechanically snap a laser lens into place centered in the laser beam axis. The focal point of the lens coincides with the tip of nozzle 34 placed in coaxial alignment with the laser beam axis. A solenoid is controlled to actuate a laser shutter to move the shutter out of the laser beam path. The laser power supply is controlled to power the laser. With the shutter open, the laser emits a beam which is focused by the lens onto the nozzle tip closure. The laser energy heats the nozzle closure and melts an opening in the closure. The opening of the nozzle closure breaches the means of maintaining the pressure differential created by the pull on bellows assembly 32.

After a predetermined exposure time depending on laser beam power, the laser shutter solenoid is actuated and moves the laser shutter across the beam, after which the laser power source is powered down.

To use the laser to reseal the opening, open nozzle 34 is repositioned in the axis for the laser beam, and the laser power supply and electrocontroller are controlled to actuate the solenoid to laser shutter to move the shutter out of the laser beam path, and also to control the laser power supply to power the laser. The laser lens is not placed in the path of the laser beam. With the shutter open, the laser emits a beam onto nozzle 34. This time the laser beam is unfocused and strikes the tip periphery of nozzle 34 as an unfocused column, heating the nozzle tip periphery to molten state. The lens shutter is then closed, and the crimping fusion of the nozzle tip is carried out as described above.

Having now described our method for sampling a liquid in a sealed volumetrically changeable receptacle having a closed nozzle and containing the liquid, and having described apparatus which is useful in practicing our invention, equivalents of invention giving the substantially the same result in substantially the same way as the functional means described for our invention will now suggest themselves to those skilled in the art, and such equivalents are intended encompassed within the spirit and scope of our invention.

We claim:

1. A method for dispensing a sample of liquid from a sealed thermoplastic container, said container comprising a volumetrically flexible chamber holding said liquid and a plurality of spaced axially vertical nozzles on the underside thereof having an inlet in fluid communication with said chamber, which comprises:

(a) rotating the container from a right side up position to an upside down position, (b) manipulating said container to increase the volume of said chamber, said steps (a) and (b) being conducted in any order before step (c), (c) creating an axial opening in one of said nozzles without decreasing the volume of the chamber, (d) rotating said container from said upside down position to a right side up position without decreasing the volume of the chamber, (e) manipulating said container to decrease the volume of the chamber, thereby to expel liquid from the chamber through said nozzle opening, (f) rotating said container from said right side up position to an upside down position, and (g) closing said opening in said nozzle.

2. The method of claim 1 in which, after step (e) and before said step (f), said container is manipulated to increase the volume in said chamber.

3. The method of claim 1 in which in step (a) said container is rotated such that the nozzle to be opened is at a sufficient angle from vertical that air trapped in the chamber gathers at the inlet to said nozzle.

4. The method of claim 1 in which said opening is created non-invasively.

5. The method of claim 4 in which said opening is created with a stream of heated air.

6. The method of claim 4 in which the opening is created with a laser beam.

7. The method of claim 1 in which said step (b) is performed by pulling on at least one other nozzle than the nozzle opened in step (c).

8. The method of claim 1 in which said container includes a bellows portion and said step (e) is performed by pushing on said bellows portion.

9. The method of claim 8 in which said a bellows portion includes said nozzles and said step (e) is performed by pushing on at least one other nozzle than the nozzle opened in step (c).

10. The method of claim 1 in which said step (g) is performed non-invasively.

11. The method of claim 10 in which said non-invasive closing step comprises:

(a) heating the opened nozzle adjacent the created opening sufficiently to make the nozzle molten, and (b) compressing the nozzle adjacent the molten portion to fuse the nozzle closed.

12. Apparatus for dispensing a sample of liquid from a sealed thermoplastic container, said container comprising a volumetrically flexible chamber holding said liquid and a plurality of spaced axially vertical nozzles on the underside thereof having an inlet in fluid communication with said chamber, which comprises:

(a) means adapted to create an axial opening in one of said nozzles of said container while said container is in an upside down position, (b) means for manipulating said container to increase the volume of said chamber before creating said opening and for manipulating said container to decrease the volume of the chamber after creating said opening, and (c) means adapted for closing said opening in said nozzle while said container is in an upside down position.

13. The apparatus of claim 12 in which said means for rotating said container from right side up to upside down comprises means for rotating said container such that the nozzle to be opened is at a sufficient angle from vertical that air trapped in the chamber gathers at the inlet to said nozzle.

14. The apparatus of claim 13 in which said means for creating an opening in said nozzle comprises means for non-invasively creating said opening.

15. The apparatus of claim 14 in which said means for creating an opening non-invasively comprises means for providing a stream of heated air.

16. The apparatus of claim 12 in which means for manipulating said container to increase the volume of said chamber comprises means for pulling on at least one other nozzle than the nozzle to be opened.

17. The apparatus of claim 12 in which said container includes a bellows portion and said means for manipulating said container to decrease the volume of said chamber comprises means for pushing on said bellows portion.

18. The apparatus of claim 12 in which said means for closing an opening in said nozzle comprises means for non-invasively closing said opening.

19. The apparatus of claim 12 in which said means for non-invasively closing an opening in a nozzle comprises:
 (a) means for non-invasively heating the opened nozzle adjacent the created opening sufficiently to make the nozzle molten, and
 (b) means for compressing the nozzle adjacent the molten portion to fuse the nozzle closed.

20. Apparatus for dispensing a sample of liquid from a sealed thermoplastic container, said container comprising a volumetrically flexible chamber holding said liquid and a plurality of spaced axially vertical nozzles on the underside thereof having an inlet in fluid communication with said chamber, which comprises:
 (a) heated air means for non-invasively melting an axial opening in said nozzle and for non-invasively heating the opened nozzle adjacent such opening sufficiently to make that adjacent portion of the nozzle molten while said container is in an upside down position at a sufficient angle from vertical that any air trapped in the chamber gathers at the inlet to said nozzle,
 (b) means for compressing the nozzle adjacent the molten portion to fuse the nozzle closed, and
 (c) means for pulling on at least one other nozzle of the container than the nozzle to be opened to increase the volume of said chamber before opening at least one nozzle in said container and for pushing on said one or more other nozzles to decrease the volume of the chamber after opening of said at least one nozzle.

* * * * *